(12) United States Patent
Mandel

(10) Patent No.: US 9,849,024 B2
(45) Date of Patent: Dec. 26, 2017

(54) APPARATUS FOR THERAPEUTIC COOLING AND WARMING OF A BODY PORTION OF A HUMAN OR MAMMAL

(75) Inventor: William R. Mandel, Nevada City, CA (US)

(73) Assignee: Oasis Medical Solutions, Nevada City, CA (US)

( * ) Notice: Subject to any disclaimer, the term of this patent is extended or adjusted under 35 U.S.C. 154(b) by 1106 days.

(21) Appl. No.: 13/703,298

(22) PCT Filed: Jun. 9, 2011

(86) PCT No.: PCT/US2011/039860
§ 371 (c)(1),
(2), (4) Date: Dec. 10, 2012

(87) PCT Pub. No.: WO2011/156643
PCT Pub. Date: Dec. 15, 2011

(65) Prior Publication Data
US 2013/0085552 A1 Apr. 4, 2013

Related U.S. Application Data

(60) Provisional application No. 61/397,324, filed on Jun. 11, 2010.

(51) Int. Cl.
*A61F 7/00* (2006.01)
*A61F 7/02* (2006.01)

(52) U.S. Cl.
CPC ...... *A61F 7/007* (2013.01); *A61F 2007/0075* (2013.01); *A61F 2007/0296* (2013.01)

(58) Field of Classification Search
CPC ...... A61F 2007/0075; A61F 2007/0296; A61F 7/007; A61B 2018/00047
See application file for complete search history.

(56) References Cited

U.S. PATENT DOCUMENTS

| | | | |
|---|---|---|---|
| 2,408,244 A * | 9/1946 | Watkins | G04B 37/005 224/170 |
| 4,585,002 A * | 4/1986 | Kissin | A61F 5/00 607/96 |
| 4,860,748 A | 8/1989 | Chiurco et al. | |
| 5,097,828 A * | 3/1992 | Deutsch | A61F 7/007 604/113 |
| 5,169,384 A | 12/1992 | Bosniak et al. | |
| 5,209,227 A | 5/1993 | Deutsch | |
| 5,531,775 A | 7/1996 | Sasaki et al. | |
| 5,580,350 A | 12/1996 | Guibert et al. | |
| 5,601,618 A | 2/1997 | James | |
| 5,628,769 A * | 5/1997 | Saringer | A61F 7/007 607/98 |
| 5,653,741 A | 8/1997 | Grant | |
| 5,674,270 A | 10/1997 | Viltro et al. | |

(Continued)

*Primary Examiner* — Jaymi Della

(57) ABSTRACT

At least one thermoelectric assembly controlled by a microprocessor and disposed on a thermal conduction pad configured to conduct energy to and from the thermoelectric assembly and adjacent the treatment area positioned with removable electronics and a breathable liner. The hot intensity, cold intensity and time delay between sequences can also be selected as well as alternating temperature sequences with both vibration and tension monitoring to promote blood flow and speed up healing.

17 Claims, 12 Drawing Sheets

(56) References Cited

U.S. PATENT DOCUMENTS

| | | |
|---|---|---|
| 5,728,058 A | 3/1998 | Ouellette et al. |
| 5,728,146 A | 3/1998 | Burkett et al. |
| 5,741,318 A | 4/1998 | Oullette et al. |
| 5,800,490 A | 9/1998 | Patz et al. |
| 5,837,005 A | 11/1998 | Viltro et al. |
| 5,860,945 A | 1/1999 | Cramer et al. |
| 5,925,072 A | 7/1999 | Cramer et al. |
| 5,970,718 A | 10/1999 | Arnold |
| 5,980,562 A | 11/1999 | Oullette et al. |
| 6,017,337 A | 1/2000 | Pira |
| 6,019,782 A | 2/2000 | Davis et al. |
| 6,020,040 A | 2/2000 | Cramer et al. |
| 6,048,326 A | 4/2000 | Davis et al. |
| 6,074,413 A | 6/2000 | Davis et al. |
| 6,091,994 A | 7/2000 | Loos |
| 6,096,067 A | 8/2000 | Cramer et al. |
| 6,102,937 A | 8/2000 | Cramer et al. |
| 6,123,717 A | 9/2000 | Davis et al. |
| 6,146,732 A | 11/2000 | Davis et al. |
| 6,336,935 B1 | 1/2002 | Davis et al. |
| 6,372,486 B1 | 4/2002 | Fripp |
| 6,567,696 B2 | 5/2003 | Voznesensky et al. |
| 6,679,908 B2 * | 1/2004 | Shimizu ............... A61F 7/02 607/109 |
| 6,699,271 B2 | 3/2004 | Clayton |
| 6,791,004 B2 | 9/2004 | Sprengard-eichel et al. |
| 6,840,955 B2 | 1/2005 | Ein |
| 6,854,426 B2 | 2/2005 | Campbell et al. |
| 6,989,471 B2 | 1/2006 | Schmidt et al. |
| 7,189,252 B2 | 3/2007 | Krueger |
| 7,238,184 B2 | 7/2007 | Megerman et al. |
| 2003/0097845 A1 * | 5/2003 | Saunders ............. A41D 13/005 62/3.3 |
| 2003/0135252 A1 * | 7/2003 | MacHold ............. A61M 25/10 607/106 |
| 2004/0133135 A1 | 7/2004 | Diana |
| 2007/0024456 A1 | 2/2007 | Currie |
| 2007/0193278 A1 * | 8/2007 | Polacek .................... A61F 7/10 62/3.2 |
| 2007/0225781 A1 | 9/2007 | Sadat et al. |
| 2008/0033518 A1 | 2/2008 | Russo et al. |
| 2008/0060374 A1 | 3/2008 | Gammons |
| 2008/0125684 A1 * | 5/2008 | Nardi ................... A61B 5/6828 602/5 |
| 2009/0069731 A1 | 3/2009 | Parish et al. |
| 2010/0268213 A1 * | 10/2010 | Manwaring ......... A61B 18/082 606/31 |
| 2011/0098610 A1 | 4/2011 | Gammons |
| 2011/0196365 A1 * | 8/2011 | Kim ...................... A61B 18/18 606/33 |
| 2013/0019873 A1 * | 1/2013 | Choi et al. ............ A61F 13/069 128/845 |

* cited by examiner

APPARATUS FOR THERAPEUTIC COOLING AND WARMING OF A BODY PORTION OF A HUMAN OR MAMMAL

CROSS REFERENCE TO RELATED APPLICATIONS

This application is a National Stage Entry of PCT/US2011/039,860, filed Jun. 9, 2011, which claims priority to and the benefit of the provisional application having Ser. No. 61/397,324 and filed Jun. 11, 2010. The provisional application and the PCT application are herein incorporated by reference in their entireties.

FIELD OF THE INVENTION

The present invention relates generally to a method and apparatus for producing a repeatable series of temperature patterns on a human body or mammal by selectively and independently controlling the heating and cooling of a Peltier-effect thermoelectric device disposed within a portable carrier.

BACKGROUND OF THE INVENTION

As people age or are deconditioned (out of shape), as is common in our society, they become more prone to exercise and repetitive motion related injuries. These injuries cause a great deal of pain and can interfere with a person's ability to function in their daily life, including loss of work time. Lateral Epicondylitis, also known as Tennis Elbow, is the term used to describe an inflammation occurring close to the humerus, a small point of the upper arm bone just above the elbow joint on the outer side of the arm. Pain can also arise in other areas of the forearm and elbow. The inflammation from tennis elbow is caused by two tendons rubbing against each other. Tendons are strong bands of tissue that connect muscle to bone. When repeatedly stressed or overused, tendons can become inflamed resulting in a painful condition called tendonitis, which can occur in tendons all over the body.

There are two common treatments for tennis elbow. One is to have a band on the forearm for compression 200 to dampen repetitive stress on the muscles and tendons. The other is to have alternating warm and cold therapy to reduce the inflammation. Commonly, the compression bands 200 is positioned either too tightly or too loosely. If the band 200 is too tight, it can restrict circulation and cause numbness. If the band is too loose, it loses its effectiveness and can even fall off. Typically, when people are first introduced to the compression band 200 treatment, they tend to over tighten the bands with the expectation of curing the condition faster. The resulting numbness can be uncomfortable and delay the healing effect of the band. Furthermore, the bands can become uncomfortable in summer months because too much heat is retained between the skin and the band.

Alternatively, hot and cold treatment typically requires two separate devices: ice packs alternating with heating pads. Although an effective treatment option, ice packs and heating pads are typically cumbersome to hold in place. With this approach, people cannot easily move around, but instead must sit and wait while receiving treatment. Gel packs may simplify treatments as they are able to retain heat and can provide cold to a treatment spot, however patient movement is still limited. To address these limitations, arm, leg, torso, and shoulder bands are now available in which the patient can apply gel packs that have been either heated or cooled to a desired treatment area. However, a limitation with this system is that gel packs do not maintain the treatment temperature for long periods of time.

SUMMARY OF THE INVENTION

The present invention relates generally to a solution to the above described treatment challenges through the use of a Thermoelectric Cooler (TEC) device and system, also generally known as a Peltier Device. Other Peltier-type devices are described and shown in U.S. Pat. No. 4,860,748 to Chiurco et al and in U.S. Pat. No. 6,097,088 to Sakuragi et al, which are hereby incorporated by reference in their entirety.

In one example embodiment of the invention, a method and apparatus are provided for producing a repeatable series of temperature patterns on a human body or mammal by selectively and independently controlling the heating and cooling of at least one Peltier-effect thermoelectric device disposed on at least one thermal conduction pad or member, which are disposed within a portable carrier or support band. In this embodiment, the thermal conduction pad facilitates heat or cool treatment (and energy distribution and application) from one thermoelectric device to the treatment area. In a related embodiment, the thermoelectric device assembly is removable from a breathable liner and/or support band to allow for cleaning and maintenance.

In one example embodiment of the invention, a method and apparatus are provided for producing a repeatable series of temperature patterns on a human body or mammal by selectively and independently controlling the heating and cooling of a Peltier-effect thermoelectric device with tension or compression monitoring, which are disposed within a portable carrier or support band 35. In a related embodiment, a vibration assembly having a vibration motor 42 is included operates with a heating cycle (or cooling cycle) of the thermoelectric device to promote healing and a faster recovery time.

In an example embodiment, both heating and cooling are provided using a passive device that will cool on one side and warm on the other when a voltage is place across it. The warm and cold sides can be exchanged by reversing the voltage on the device. Distribution of both hot and cold treatments in the TEC is performed by thermal conduction of a liquid and or a gas through a closed system with a valve. In one example embodiment, the present invention provides a mobile therapeutic treatment device that includes an attachment band or member that automatically provides alternating hot and cold treatment on a pre-programmed schedule without requiring additional action by the user. In this example embodiment, the band itself includes air vents 9 to reduce sweating and further includes a tension (or compression) monitoring system to prevent over-tightening of the band 200 member over or near the treatment region.

In various example embodiments of the present invention, significant improvements in convenience and efficiency are provided over currently available treatment options. Further, several embodiments of the present invention have other applications such as reducing swelling in the body that is caused by trauma, sprain, bursitis or overuse. Affected areas can be almost anywhere on the body such as but not limited to arms, legs, back, and neck, wherever heat/cold treatment is desired. These and other challenges are addressed by the various embodiments of the present invention.

In one example embodiment of the present invention, a band is used to wrap any area of the human body to deliver warm and cooling therapy to the skin and underlying tissue and muscle. The band also allows air to flow through itself while continuously monitoring band tension. Furthermore, the treatment system is programmable through an intuitive user interface that will allow the user to perform routine daily activities while undergoing hot and cold therapy.

In yet another related embodiment the device is mobile and ergonomically friendly device and allows hot and cold therapy to be distributed over a larger treatment area using at least one thermal conduction pad or member via fluid dynamics through either by convection or a pump method. Small valves in the fluid path with the conduction member ensure flow direction as the device alternates between hot and cold therapy.

In yet another example embodiment, the user interface is logical and allows for easy setting identification wherein Red is for hot treatment and Blue is for cold treatment or temperature. Using markings of "C" for cold and "W" for warmth and a "clock" symbol for time or duration of treatment also ensures easy identification of controls. This example system delivers continuous hot, continuous cold, and intermittent hot and cold as programmed by the user. In this example embodiment, the band member is breathable, or made out of a breathable material, thereby reducing sweating and itching on or about the treatment area. The electronic assemblies are removable for easy routine cleaning. In this example embodiment, monitoring band tension (or compression) removes the unknown factor of whether the band 200 is too tight and the use of lithium battery technology (or other rechargeable battery source or use of solar cells) allows this device to be mobile. Finally, using passive electronics to switch polarity on the Peltier device results in no moving parts and long device life.

Advantageously, the various embodiments of the present invention provide for adding communication devices for wired or wireless communications between two or more separate physically distinct apparatus to promote alternative heating/cooling cycles as part of the treatment regimen; incorporating temperature measuring devices or sensors (thermistors, thermocouples, etc.) to sense temperature and prevent injury to the patient from a device that is too hot or too cold; incorporating ventilation holes or slits in the support band; and promote warm wet heating therapy by accommodating a moist towelette, cloth or other fabric.

In another aspect of the present invention, an apparatus for treating an area of a human body by creating a series of temperature patterns on surface of the body adjacent the treatment area, said apparatus comprising a thermal conduction member and a at least one thermoelectric means for producing a temperature change in response to an electrical input disposed on the thermal conduction member. The apparatus further includes a metallic member interposed between said thermoelectric means and the thermal conduction member and at least one heat sink member disposed on said thermoelectric means. The apparatus further includes electronic controller means connected to said thermoelectric means for controlling said thermoelectric means so that said thermoelectric means creates changeable temperature patterns on a treatment area; said electronic controller means adapted to be connected to a portable power source; and therapy control means connected to said electronic controller means for controlling the time and intensity of a temperature produced by said thermoelectric means before reversing a temperature gradient for said thermoelectric means. In a related embodiment, the metallic member interposed between said thermoelectric means and the thermal conduction member is omitted.

In yet another aspect of the present invention, a method of treating a portion of the human body pain by creating a series of temperature patterns on the surface of the body adjacent a treatment area, said method comprising the steps of (a) placing a thermal conduction member on the surface of the body adjacent the treatment area, the thermal conduction member having thermoelectric means disposed thereon and one heat sink member disposed on said thermoelectric means and (b) controlling said thermoelectric means via electronic controller means to create changeable temperature patterns on a treatment area, said electronic controller means and thermoelectric means adapted to be connected to a portable power source. The method further includes the steps of (c) controlling said electronic controller means via therapy control means thereby controlling a time and intensity of a temperature produced by said thermoelectric means before reversing a temperature gradient for said thermoelectric means; and (d) monitoring at least one characteristic selected from the group consisting of: compression of thermal conduction member on the body surface; duration of a selected temperature treatment; and intensity of a selected temperature treatment.

In a related aspect of the invention, a vibration assembly is connected to the metallic member and is adapted to generate vibrations when heat is being applied to the treatment area. In another related embodiment, a synchronization assembly is coupled to the microcomputer, the synchronization assembly further including at least two communication modules adapted to be connected to at least two separate physically distinct apparatus thereby generating alternating temperature patterns to promote blood flow in the treatment area. In yet another related embodiment, the thermal conduction member is comprised of a plurality of tubes for conducting a fluid through the thermal conduction member with at least one thermal flow control member selected from the group consisting of: a one-way valve, a one-way value and a pump, and a pump. In yet another embodiment, a visual indicator is included for time and temperature selected from the group consisting of an LED, a time clock button, and a push button mechanism disposed adjacent said electronic controller means.

BRIEF DESCRIPTION OF THE DRAWINGS

The same elements or parts throughout the figures of the drawings are designated by the same reference characters.

DETAILED DESCRIPTION OF THE PREFERRED EMBODIMENTS

The following description is meant to be illustrative only and not limiting. Other embodiments of this invention will be apparent to those of ordinary skill in the art in view of this description.

Figure 1:
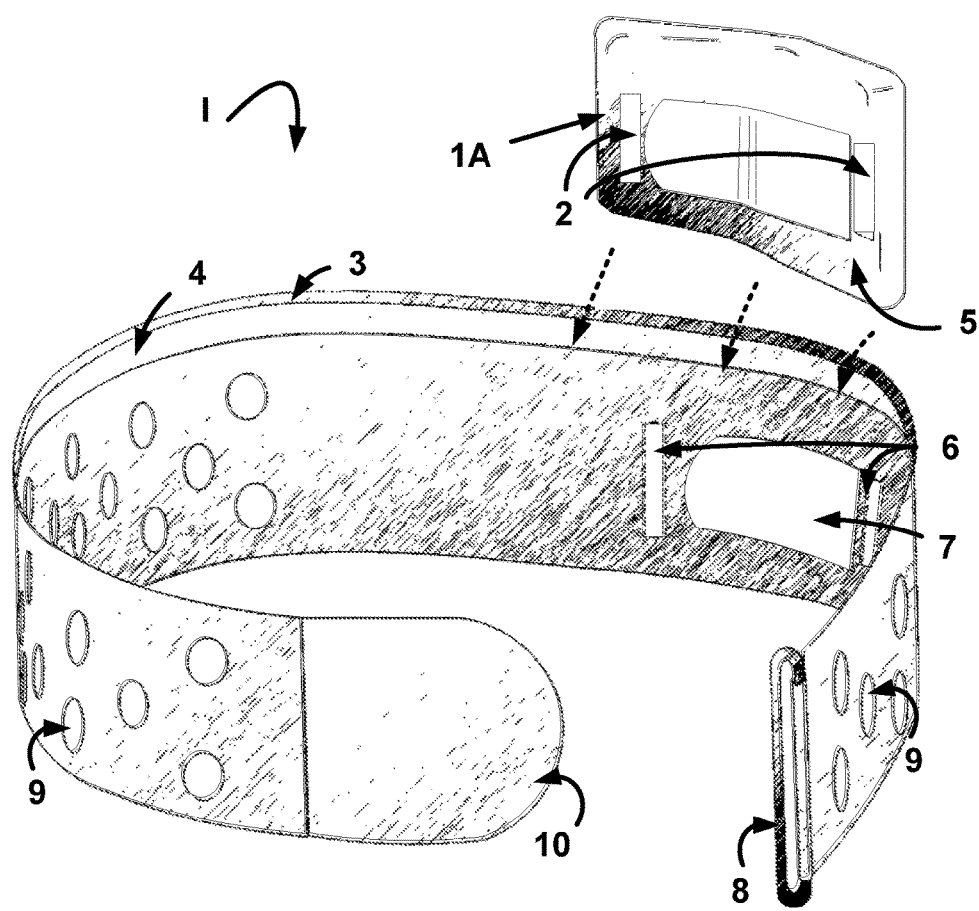
FIG. 1 is a perspective, exploded view of an embodiment of a therapy band member with an electronic assembly according to the present invention.

Referring generally to FIG. 1, there is depicted a perspective view of a pouch-style therapy band or support member 1 which shows how an electronic unit 1A fits into the band and is held in place with a set of hook and loop fastening strips 2 and a set of corresponding fasteners 6, which a fastening strip 3 secures and closes a pouch structure 4.

In this example embodiment, a therapy plate 5 is placed over a window 7 (in which the therapy plates rest) while a set of cooling holes 9 (or slits) in the band allow for ventilation. A tip 10 (having a fastening structure thereon) of the band is placed through a clasp tensioner loop 8 to hold band 1 in place and to adjust the tension or compression of the band over the treatment site. In other example embodiments, band member 1 is a vest, a pouch, a pouch with strips, a backpack or the like that allows for portably supporting the therapy device of the present invention.

Figure 2:
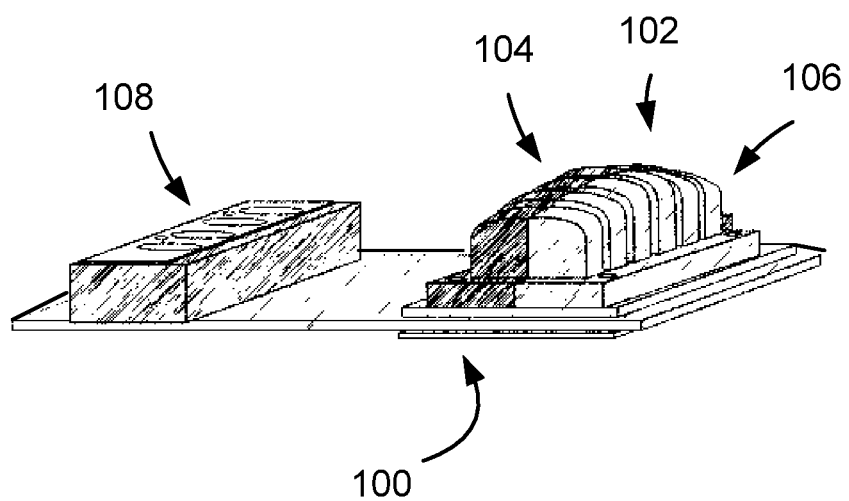
FIG. 2 is a perspective view of a Peltier assembly according to the present invention.
Figure 8:
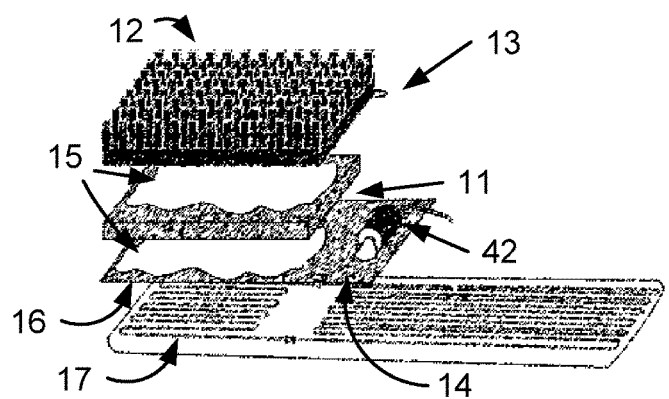
FIG. 8 is an exploded view of the therapy band assembly with a vibration assembly according to the present invention.

Referring now to FIGS. 8 and 2, respectively, there are depicted an exploded Peltier therapy assembly 11 and a removable assembly 100 according to the teachings of the present invention. Referring particularly to FIG. 8, assembly 11 further includes a heat sink member 12 disposed on the outside of therapy band 1 that is configured to dissipate both warmth and cold depending on the cycle of the therapy. An epoxy or adhesive layer 15 holds three parts together: heat sink 12 to a Peltier device 11A, and Peltier device 11A to a thermal conducting mesh 16 (which can also be a metal braid, mesh or plate to conduct both heating and cooling). Epoxy material can be conductive material, such as heat conductive epoxy and/or thermal grease. Thermal conducting mesh 16 attaches to a thermal distribution pad 17 which delivers the therapy to the skin and conducts the energy to a thermal measuring or sensing device (such as a thermistor or a thermocouple) so that a microprocessor, which is coupled to the temperature measuring or sensing device, can adjust to the temperature by turning the temperature on and off using Pulse Width Modulation (see FIG. 10 for sample waveforms). Therapy assembly 11 further includes a point of contact of a temperature sensing (or measuring) device 13 and a second point of contact for a temperature sensing (or measuring) device 14 (such as thermistors, thermocouples or the like).

Referring now to FIG. 2, there is illustrated a perspective view of a heat sink assembly 100 of the therapy band assembly according to the present invention. In this example embodiment, a heatsink assembly 102 is comprised of two identical halves, cooling heatsink 104 and warming heatsink 106. One half will be anodized blue aluminum (104) and the other will be anodized red aluminum (106) for ease of use and visual recognition for the user. These and various embodiments are configured to be disposed on thermal distribution pad 17.

Figure 3:
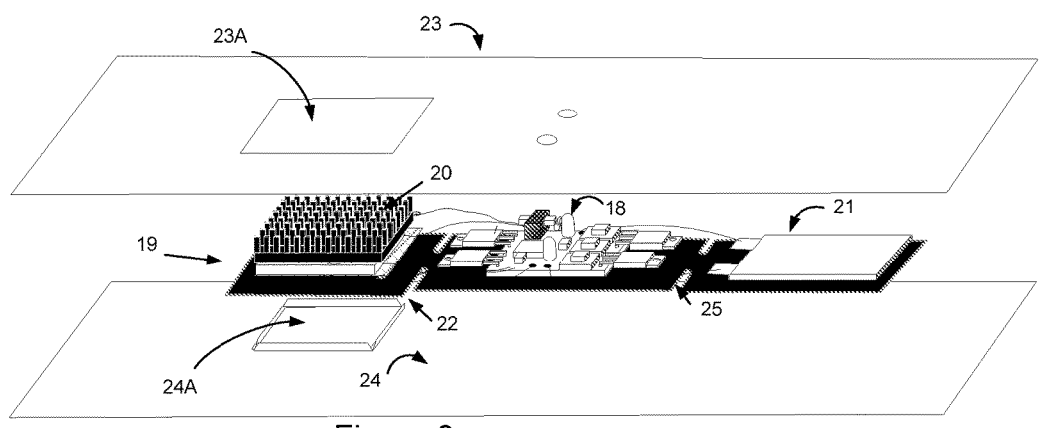
FIG. 3 is an exploded view of an electronic assembly according to the present invention.

Referring now to FIG. 3, there is shown an exploded view of the components of electronic assembly 1A (that forms part of the therapy band) which includes an electronic circuit board 18 and a battery 21 which are mounted on a semi-ridged base or plate 25. The bottom of an enclosure formed by a top plate 23 and a bottom plate 24 (both of which could be made of flexible plastic) contains flaps that go through a window 24A. Semi-ridged base 25 is mounted to the bottom of electronic circuit board 18 and is attached to the edges of therapy device assembly 19 with epoxy or some other adhesive. (Therapy device assembly 19 is as described in more detail in the specification associated FIG. 2). In this example embodiment, therapy device assembly 19 is adapted to protrude through a window 23A and window 24A and includes a heat sink thermal sensing/reading/measuring device 20 and a thermal plate sensing/reading/measuring device 22 adapted to provide temperature readings for cold and warm temperatures, respectively. Circuit board 18 is electrically coupled to power source 21, which may be a portable power sources such as a battery, and to device assembly 19 on the other side.

Figure 4:
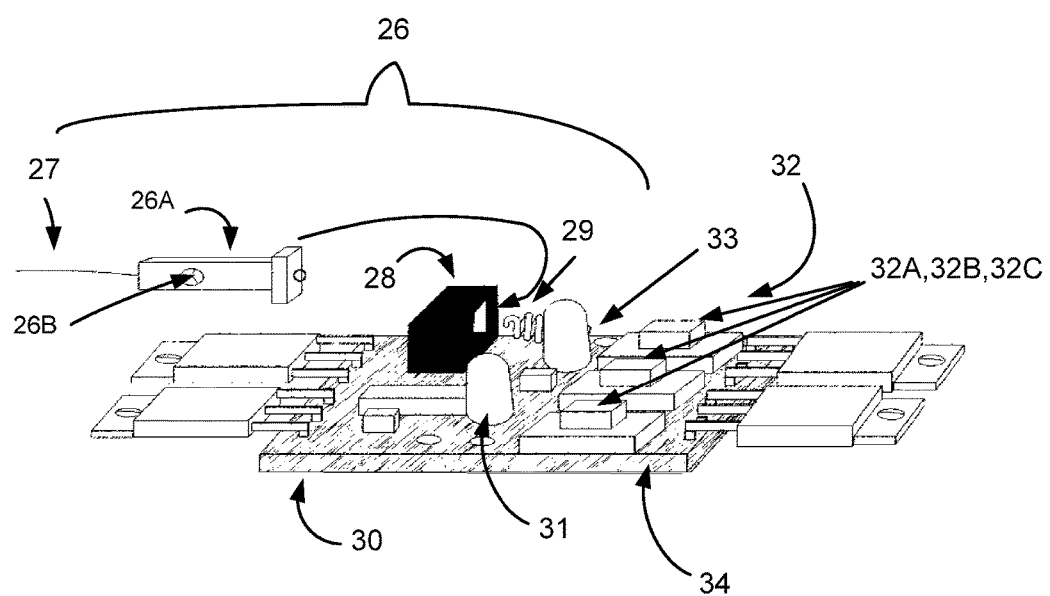
FIG. 4 is a perspective view of a tension monitoring device according to the present invention.

Referring now to FIG. 4, there is shown a mechanical tension (or compression) assembly 26, integrated with circuit board 18, which is adapted to be electrically and mechanically coupled to therapy device assembly 19. In this example embodiment, tension assembly 26 includes a tension slide member 26A that is placed in a flag sensor 28 and is attached to a spring member 29. A tension wire 27 is attached to a far point on the plastic base and the other end is attached to tension slide member 26A. Tension assembly 26 further includes a printed circuit board (PCB) 30 with electronics thereon and includes a blue LED 31, a red LED 33 and a set of interface buttons 32A-32C disposed on a set of bases 34 that are disposed on board 30. As the therapy band is cinched up (or put on user), the tension wire is pulled which in turn pulls tension slide 26A. If the therapy band is tightened correctly, flag sensor 28 will have no light passing through and the system will identify that the band is not too tight. If the band becomes too tight, a hole 26B in tension slide 26A will allow light to pass through and the system will identify that the band is too tight and in turn the red LED 33 will flash.

Figure 6:
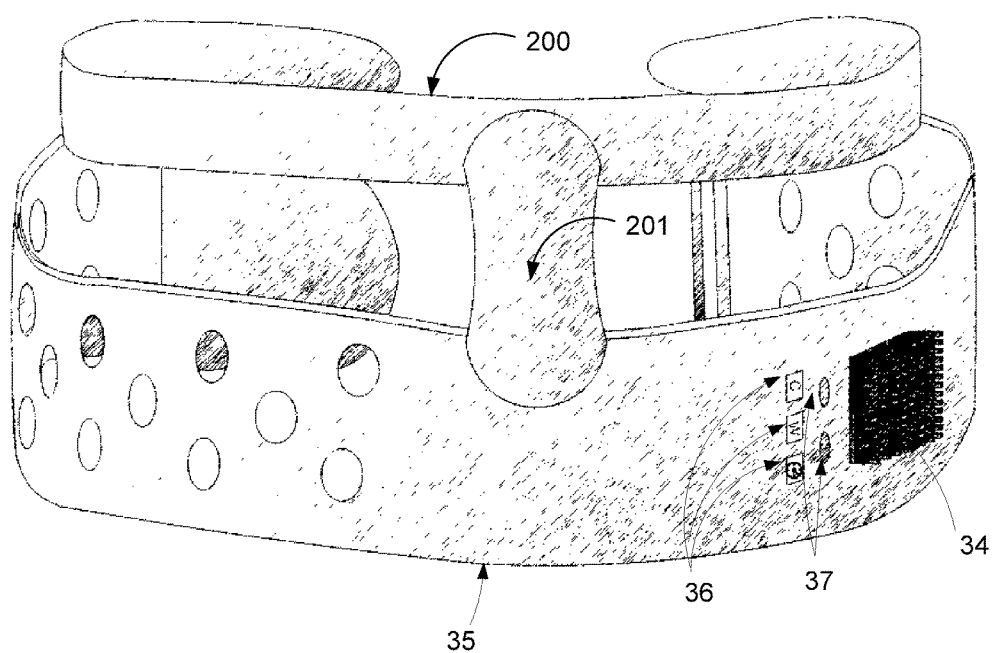
FIG. 6 is a perspective view of the therapy band assembly according to the present invention.

In one example embodiment of a user interface 32 of the therapy band, there are 3 buttons 32A, 32B and 32C and 2 LEDs 31 and 33 (another example is illustrated in FIG. 6). Each button is labeled and has a different color: red, blue, and green. A red button 32A controls the intensity of the warmth, a blue button 32B controls the intensity of the cold, and a green button 32C controls the duration of the therapy interval. The two LEDs are Red 33 and Blue 31 indicating warming or cooling activity.

TABLE A

| Button Event Table | First press | Second Press | Third Press | Fourth Press |
| --- | --- | --- | --- | --- |
| Red Button | Set Low Intensity. One Red Blink. | Set Medium Intensity. Two Red Blinks. | Set High Intensity. Three Red Blinks. | Set Warmth to Off. No Red Blink. Resets so that the next press is the first. |
| Blue Button | Set Low Intensity. One Blue Blink. | Set Medium Intensity. Two Blue Blinks. | Set High Intensity. Three Blue Blinks. | Set Cold to Off. No Blue Blink. Resets so that the next press in the first. |
| Green Button | 3 Minute Duration. Both LEDs Blink Once. | 5 Minute Duration. Both LEDs Blink Twice. | 10 Minute Duration. Both LEDs Blink Three times. | Continuous if either the warmth is off or the cold is off. Neither LED blinks. Resets so that the next press in the first. |

In this example embodiment, in order to obtain alternating warmth and cold, the therapy system blinks 1 to 3 Red blinks, 1 to 3 Blue blinks, and 1 to 3 Green blinks. In another embodiment, to obtain alternating warmth, the system blinks 1 to 3 Red blinks, 0 Blue blinks, and 1 to 3 Green blinks. In yet another embodiment, to obtain alternating cold, the therapy system blinks 0 Red blinks, 1 to 3 Blue blinks, and 1 to 3 Green blinks. In yet another embodiment, to obtain continuous warmth, the system blinks 1 to 3 Red blinks and 0 Blue blinks, and a duration of 0 Green blinks. In yet another embodiment, to obtain continuous cold, the system blinks 0 Red blinks and 1 to 3 Blue blinks, and a duration of 0 Green blinks.

In a related embodiment of the user interface, there is included a set of 4 interface buttons and 2 LEDs. Each button is labeled and has a different color: red, blue, green, and orange. The red button controls the intensity of the warmth, the blue controls the intensity of the cold, the green controls the duration of the cold therapy interval, and the orange controls the duration of the warm therapy interval. The two LEDs are Red and Blue indicating warming and cooling activity, respectively.

blinks, and 1 to 3 Orange blinks. To obtain continuous warmth, the system blinks 1 to 3 Red blinks and 0 Blue blinks, 1 to 3 Green blinks, and 0 Orange blinks To obtain continuous cold, the system blinks 0 Red blinks and 1 to 3 Blue blinks, 0 Green blinks, and 1 to 3 Orange blinks.

Figure 5A:
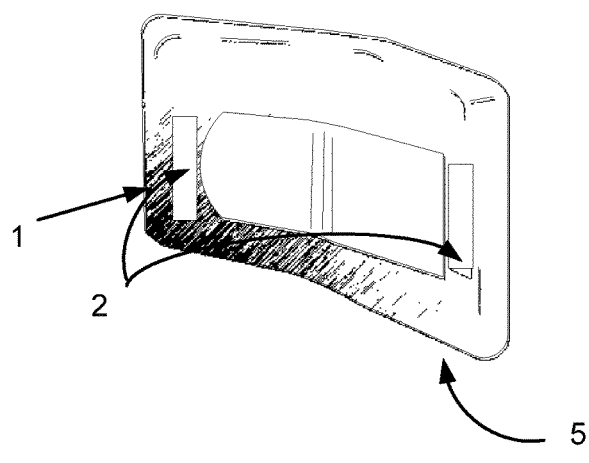
FIGS. 5A and 5B are front and back views of the electronic assembly according to the present invention.
Figure 5B:
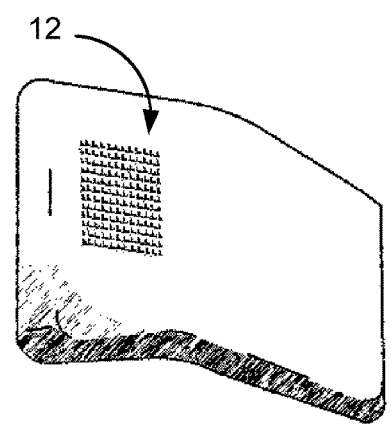

Referring now to FIGS. 5A-5B, there are illustrated front and back views of electronic unit 1A. Fastening strips 2 are used to hold the electronic unit in place so that therapy plate 5 remains in the correct position. In this example embodiment, heat sink 12 protrudes through the therapy band and is outwardly facing (see FIG. 5B). In this example embodiment, electronic unit is removable from the therapy band so that the band can be cleaned without damage to the electronics.

Referring now to FIG. 6, there is illustrated a perspective view of an example embodiment of an assembled therapy band 35 of the present invention. In particular, FIG. 6 illustrates the exterior of the band using a 3 button configuration (36A-36C). A blue button 36A labeled "C" controls the cold intensity, a red button 36B labeled "W" controls the warm intensity and a green button 36C labeled ☺ (i.e., clock) is the duration time as described in Tables A and B

TABLE B

| Button Event Table | First press | Second Press | Third Press | Fourth Press |
| --- | --- | --- | --- | --- |
| Red Button | Set Low Intensity. One Red Blink. | Set Medium Intensity. Two Red Blinks. | Set High Intensity. Three Red Blinks. | Set Warmth to Off. No Red Blink. Resets so that the next press is the first. |
| Blue Button | Set Low Intensity. One Blue Blink. | Set Medium Intensity. Two Blue Blinks. | Set High Intensity. Three Blue Blinks. | Set Cold to Off. No Blue Blink. Resets so that the next press in the first. |
| Green Button | Cold temperature is set to 3 Minute Duration. Both LEDs Blink Once. | 5 Minute Duration. Both LEDs Blink Twice. | 10 Minute Duration. Both LEDs Blink Three times. | Cold is off. Neither LED blinks. Resets so that the next press in the first. |
| Orange Button | Warm temperature is set to 3 Minute Duration. Both LEDs Blink Once. | 5 Minute Duration. Both LEDs Blink Twice. | 10 Minute Duration. Both LEDs Blink Three times. | Warmth is off. Neither LED blinks. Resets so that the next press in the first. |

In this and the following example embodiments, in order to obtain alternating warmth and cold therapeutic treatments on the user, the therapy system blinks 1 to 3 Red blinks, 1 to 3 Blue blinks, 1 to 3 Green blinks, and 1 to 3 Orange blinks. To obtain alternating warmth, the system blinks 1 to 3 Red blinks, 0 Blue blinks, 1 to 3 Green blinks, and 1 to 3 Orange blinks. Similarly to obtain alternating cold, the system blinks 0 Red blinks, 1 to 3 Blue blinks, 1 to 3 Green above. There are 2 LED indicator ports (37A, 37B), one blue 37A and one red 37B, which flash as described in Tables A and B above. In this example embodiment, arm band 35 shows ventilation holes 9 and the placement of thermal conductor (or heat sink) 12. The thermal conductor radiates warmth when the band is cooling and absorbs heat when the band is warming. In another example embodiment, the heat sink is a braided metal sheet. In related embodiments, arm band 35 is configurable to be, but is not limited to, a waist band, a shoulder band or a pouch or back pack or fanny pack to accommodate other parts of the human body. FIG. 6 also shows the tendon compression member bridge 201 which connects the assembled therapy band 35 with the tendon compression member 200.

In various related embodiments, the following advantages are provided, there include: A) having 4 buttons on the user interface: Cooling, Warming, Cooling Time, Warming Time; B) having 3 to 4 LEDs on or about the user interface: one for each button described in 1; C) having the holes/slits for cooling can vary in size for comfort; D) a knit fabric net or layer is placed between the inner facing and the skin to retain air circulation and comfort; and E) having a tension device, such as a strain gauge or piezo-electric device, can be used for measuring tension or compression support band 200.

Figure 7:
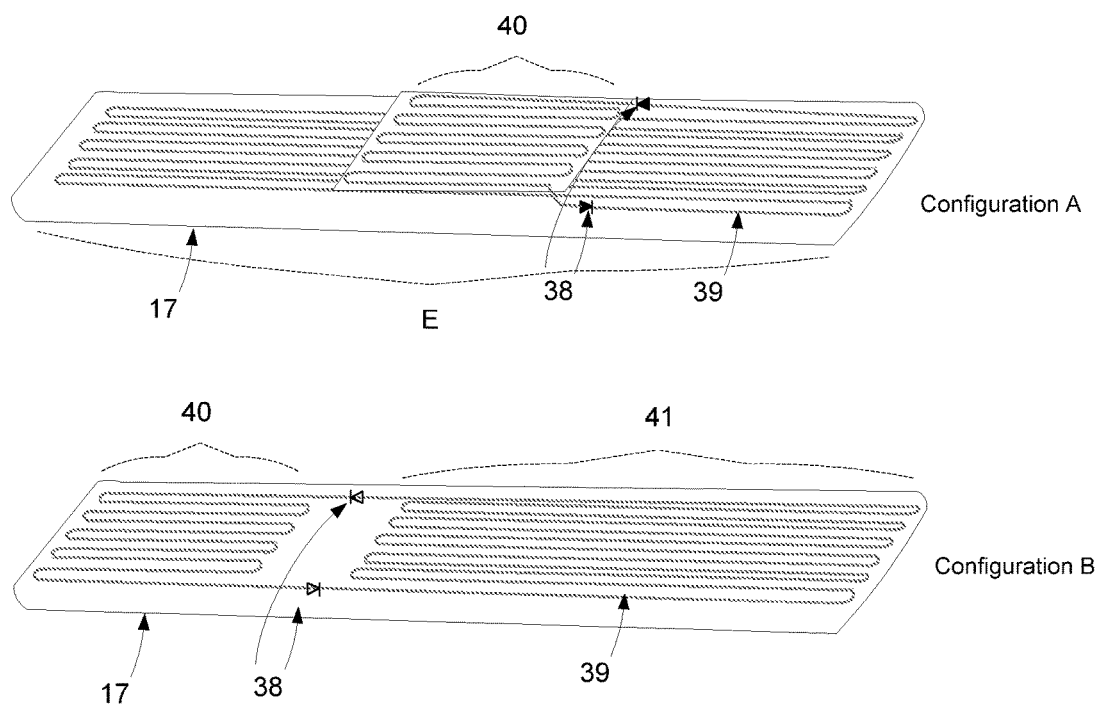
FIGS. 7A and 7B are perspective views of other embodiments of thermal transfer pad or distribution members according to the present invention.

Referring now FIGS. 7A and 7B, there are illustrated various example embodiments of thermal transfer (or conduction) pads or members 17A and 17B according to the present invention. In one example embodiment of transfer pad configuration 17A, a Peltier device assembly is disposed on portion or area 40 of pad 17A and it heats and cools this area. Thermal conduction within pad 17A forces a liquid or a gas through a set of valves 38 and into a therapy delivery area 41. The flow path is indicated by the value direct as show in FIG. 7A.

In a related embodiment, thermal transfer (or conduction) pad configuration 17B moves the thermal energy horizontally from area or portion 40 to a thermal expansion area 41. In transfer pad configurations 17A and 17B, the pad includes a series of small flexible tubes 39 whose flow is based on thermal conduction. In a related embodiment, the transfer pad has one tube and one valve to control fluid flow and energy transfer. The cooling or warming media in the tubes can be either a gas, a liquid or a liquid with a low boiling point which will enhance the flow. A third transfer pad configuration consists of utilizing a simple gel pack (or hot and cold water packs or other fluids that retain heat or cold) to conduct the thermal energy.

Referring now to FIG. 8, there is shown a Peltier assembly according to the present invention similar in construction to assembly 19 described in FIG. 2 and the associated specification. In this example embodiment, a vibrator mechanism 42 is added to the therapy device so as to assist with penetration and the soothing and loosening of tight muscles during the heat cycle. In this example embodiment, vibrator 42 is built into assembly device 19 such that it is passes through contacting plate 14. Vibrator mechanism 42 includes a vibrator motor that is configured to be turned on and off from a microprocessor during any phase of the heating and cooling cycle. Furthermore, the vibrating intensity can be controlled with a pulse width modulation (PWM) signal. In this example embodiment, an additional key on the user interface controls the vibration (see section on Mode in Table C below). The vibrator motor includes an offset balance attached to plate 16.

Figure 9:
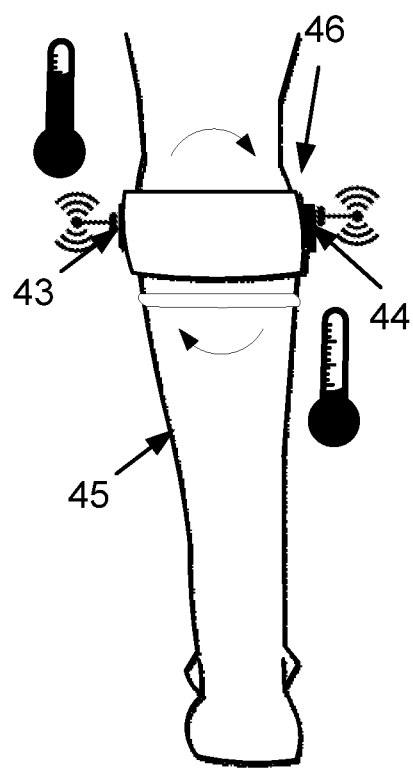
FIG. 9 is a view of a human leg with a synchronization device included with a therapy device according to the present invention.

Referring now to FIG. 9, there is shown a human leg 45 with a synchronization device 46 included with the therapy device according to the present invention. Disposed on leg 45 are two separate physically distinct apparatus 43 and 44 with communications capabilities that are adapted to communicate with one another or alternatively to other apparatuses. In this example embodiment, synchronization device 46 disposes two separate physically distinct apparatus 43 and 44 about 180 degrees from each other. If more than one therapy unit is used to treat a certain area, the therapy units are configurable to be synchronized to work either together or opposite from each other. Synchronization between modules 43 and 44 (or more) is achievable either through wired or wireless technology (such as Bluetooth or other RF technology). Having more than one unit working together can increase the power and better distribute the hot and cool therapy to the treatment area. Having more than one therapy unit working opposite can more effectively draw the blood to and from the affected area to increase circulation and hence reduce swelling and promote healing. In this example embodiment, the synchronization feature uses an additional key that is labeled as a mode key.

The mode key switches between vibration and synchronization. See the following table.

TABLE C

| Key Press | Vibration | Synchronization | LED Flashes |
|---|---|---|---|
| Initially | Off | Together | 0 |
| First Press | On | Together | 1 |
| Second Press | Off | Opposite | 2 |
| Third Press | On | Opposite | 3 |
| Forth Press | Off | Together | 0 |

The forth press returns the system back to the initial settings.

This key has the symbol:  which represent a dial.

Figure 10:
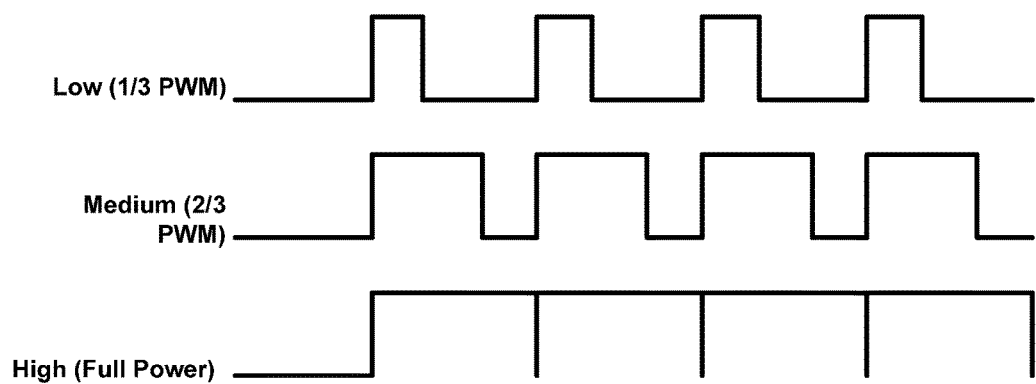
FIG. 10 illustrates various pulse trains at various power levels that control various elements of a therapy device according to the present invention.

Referring now to FIG. 10, there is illustrated various pulse trains at various power levels that change the various operating characteristics of the therapy band device according to the present invention. In one example embodiment, the pulses are used to drive 1, 2, and 3 flashes to determine the changes in treatment state. In another related embodiment, the pulse modulation drives an interface to change the intensity of one or more LEDs such as by changing the pulse width modulation (PWM) or by resistor values on the LED. In this example embodiment, a first flash is low intensity, a second is medium intensity, and a third would be the high intensity. In general, the intensity of the LED would match the intensity of the therapy provided.

In a related embodiment, the therapy device of the present invention is configurable to provide warm wet heat. Warm wet heat is desired for adding moisture to an affected area which is accomplished by inserting a wet towelette or fabric, about the same size as the contact area, between the device contact plate and the human skin.

Figure 11:
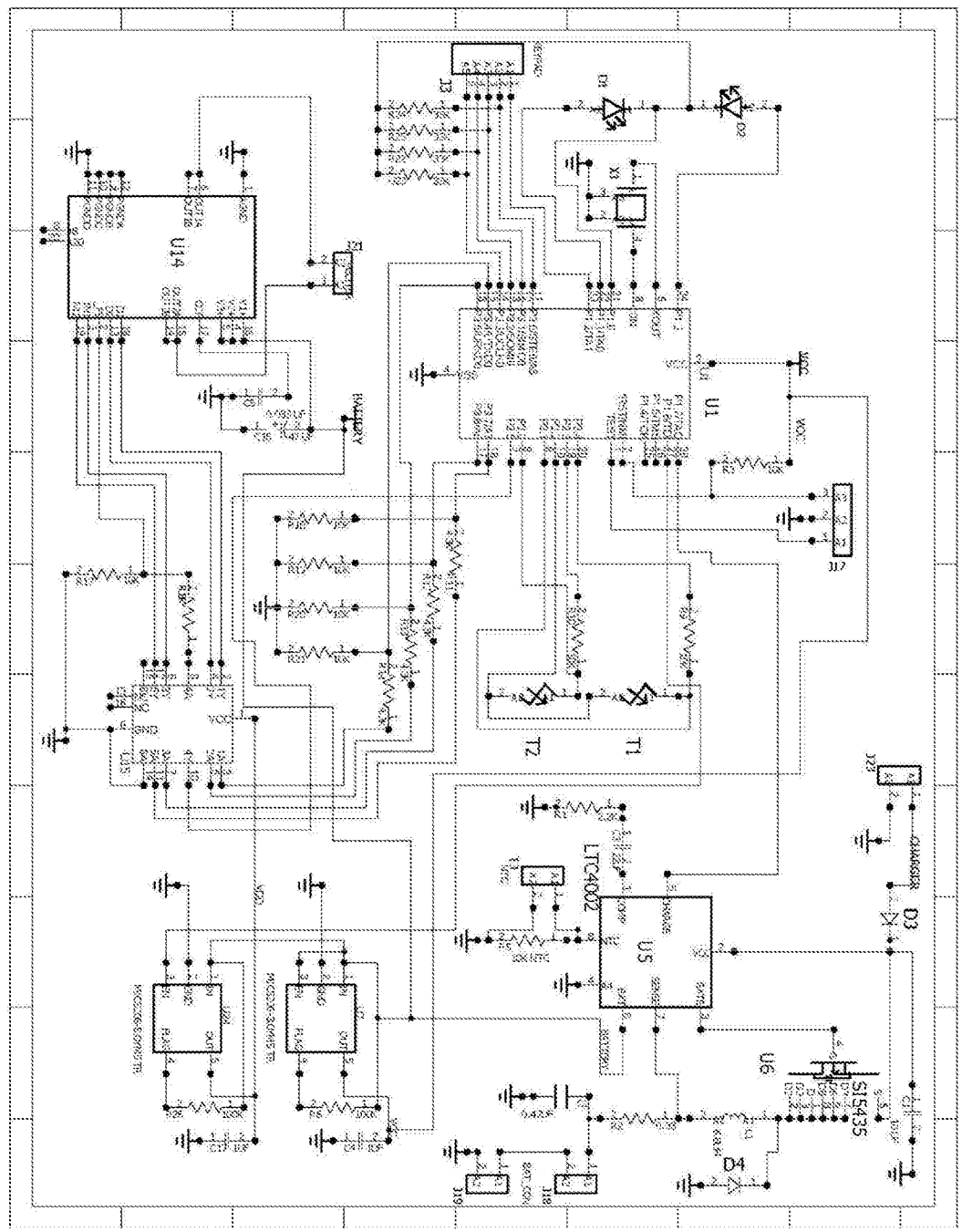
FIG. 11 is a schematic view and circuit of the microprocessor assembly according to the present invention.

Referring now to FIG. 11, there is shown an example embodiment of a schematic of the electronics located on circuit board 18, which is located in an enclosure along with the battery shown in FIG. 11 (and FIG. 3). The battery utilizes polymer lithium Ion technology, which has a very compact size. FIG. 11 includes various sections for operation: U5 is the battery charge circuit, U7 and U24 are voltage regulators, T1 and T2 are the thermistors to monitor the temperature on either side of a peltier device embodiment described herein. U14 is a DC motor driver that allows a microprocessor to turn on any one of the peltier devices described herein into either a positive or negative voltage thereby allowing alternating between hot and cold temperature treatment to be administered to the patient. U1 is the main micro-controller that drives the system. In this example embodiment, a Texas Instrument MSP430 is used as the controller. This is a low power device that has extreme low sleeping power consumption. Port 3 (P3) pins 11 through 14 read the keypad. Port 1 pin 3 and Port 1 pin1 turn on and off the LEDs. Port 1 and Pin 0 allows the system to turn the ground on and off to these devices and results in an extremely low power mode to occur by reducing leakage voltage. Similarly, Port 2 pin 2 can turn on and off the ground to the thermal couples, resulting in reducing leakage current through this part of the circuit. The thermal couples are read through an analog to digital converters that are built in to the microprocessor. Because the microprocessor is powered (VCC) with the same power to the analog to digital converters it results in a stable reading as the voltage reduces over time due to battery discharge. U15 is used to transition from a low voltage of the microprocessor to the higher voltage of the motor driver.

Figure 12:
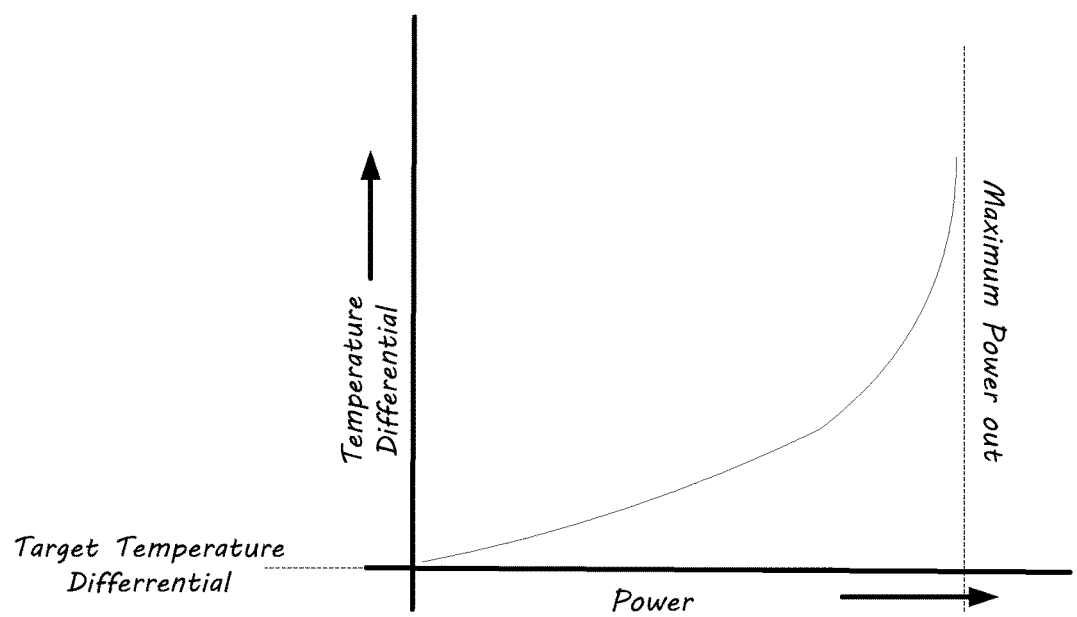
FIG. 12 is a graph of the relationship between Temperature Differential and Power according to an embodiment of the invention.

Referring now to FIG. 12 is a graphic representation of the relationship between temperature differential and power supply to the Peltier device. As the temperature differential gets smaller the power gets smaller as well. Similarly, as the temperature differential gets larger the power gets larger.

Figure 13:
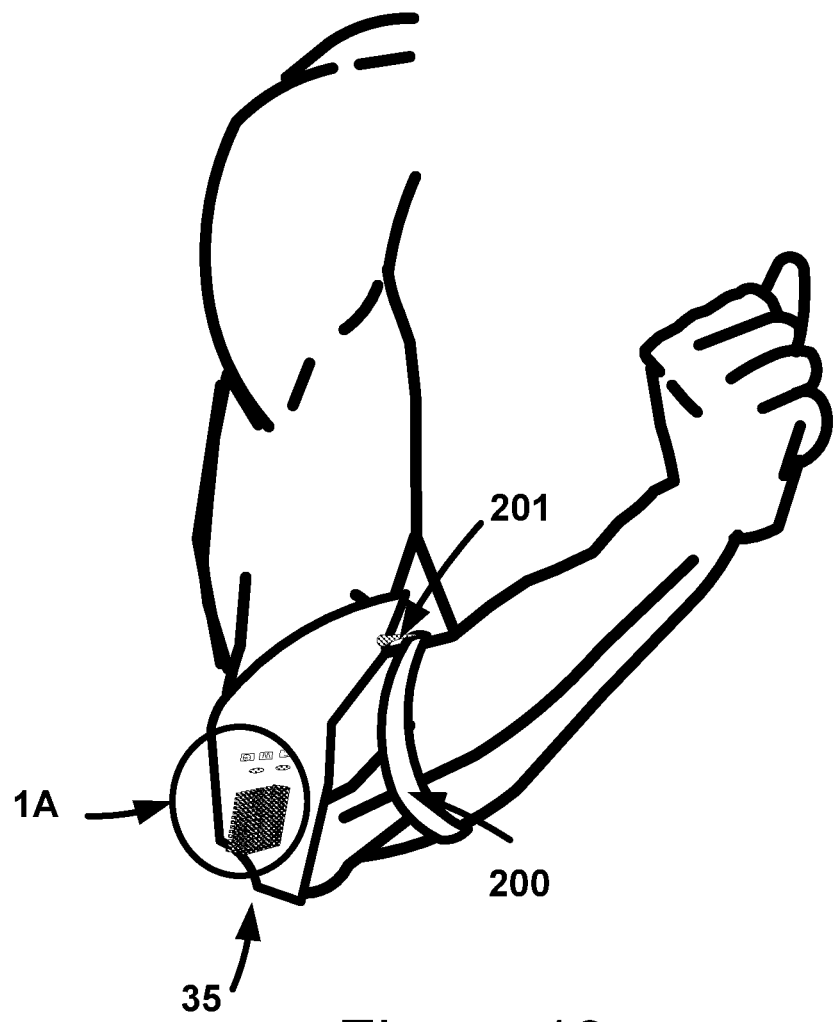
FIG. 13 is a view illustrating how the apparatus might fit on the elbow and the placement of the tension strap according to an embodiment of the invention.

Referring now to FIG. 13 depicted the apparatus affixed to an arm with the positioning of assembled therapy band 35 and tendon compression member 200. FIG. 13 also shows the tendon compression member bridge 201 which connects the assembled therapy band 35 with the tendon compression member 200.

All patents, patent applications, and publications cited herein are hereby incorporated by reference in their entirety as if individually incorporated.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. An apparatus for treating pain in an area of a human body by creating a series of temperature patterns on a surface of the human body over a treatment area, said apparatus comprising:
    a thermal conduction member;
    a power source;
    a Peltier device for producing a temperature change in response to an electrical input, said Peltier device disposed on said thermal conduction member;
    a metallic member interposed between said Peltier device and said thermal conduction member;
    a heat sink member disposed on said Peltier device;
    a programmable microcomputer connected to the power source and the Peltier device, the programmable microcomputer adapted to control application of power to the Peltier device so as to control heating and cooling of the Peltier device, wherein control by the programmable microcomputer is achieved by generating power signals which have varying pulse trains of predetermined power and modulation levels, and wherein said programmable microcomputer is configured to control the Peltier device to produce the series of temperature patterns which can be applied to said treatment area, wherein a first predetermined temperature pattern of the series of temperature patterns comprises a first predetermined time period of warm temperature of a first predetermined intensity and a second predetermined time period of cool temperature of a second predetermined intensity;
    a synchronization assembly coupled to the programmable microcomputer and the Peltier device, said synchronization assembly is adapted to coordinate operation so that the first predetermined temperature pattern and a second predetermined temperature pattern of the series of temperature patterns are generated by the programmable microcomputer and provided to the Peltier device, wherein the first predetermined temperature pattern and the second predetermined temperature pattern are alternating with respect to one another, to thus promote blood flow in the treatment area;
    a support band member configured to hold the apparatus in place such that the Peltier device and the heat sink member are positioned on the treatment area, and configured to support a tendon compression member adjacent to the treatment area with the power source; and
    a tension monitoring assembly comprising an optical system with an optical interruption mechanism.

2. The apparatus of claim 1, wherein:
    said programmable microcomputer is adapted to control the application of power by the power source to said Peltier device in relation to a temperature differential between a temperature of the Peltier device and one of the warm temperature of the first predetermined intensity and the cool temperature of the second predetermined intensity.

3. The apparatus of claim 1, wherein the thermal conduction member is comprised of at least one tube to conduct a fluid through said thermal conduction member that is woven back and forth to create a thermal distribution pad and at least one one-way valve for controlling a convection flow of the fluid through the thermal conduction member.

4. The apparatus of claim 1, further comprising:
    a user interface including at least one button to select the series of temperature patterns in response to user input, a first LED that is activated in response to the selection of the first predetermined time period of warm temperature and a second LED that is activated in response to the selection of the first predetermined time period of cool temperature.

5. The apparatus of claim 1, further including a removable assembly comprising the Peltier device and the heat sink member, the removable assembly adapted to facilitate cleaning and maintenance thereof.

6. The apparatus of claim 1, further comprising a moisture delivery system comprising at least one moisture-absorbing material element, wherein the moisture delivery system is adapted to be disposed and located on the thermal conduction member and the at least one moisture-absorbing material element is adapted to release moisture during heating of the Peltier device.

7. The apparatus of claim 1, further comprising a vibration assembly adapted to generate vibrations during heating of the Peltier device and connected to a front skin contacting plate of the metallic member.

8. The apparatus of claim 7 further comprising a tensioner with the support band member to hold the apparatus against the treatment area.

9. The apparatus of claim 1, wherein said programmable microcomputer is configured to utilize feedback from at least two temperature sensors, one to monitor a front facing metallic member and one to monitor the heat sink in order to adjust a temperature setting to reach and maintain desired temperatures.

10. The apparatus of claim 1, wherein the programmable microcomputer is adapted to collect tension-compression and temperature sensor data from the tension monitoring assembly and as at least one temperature sensor wherein the programmable microcomputer further comprises a system to communicate the tension-compression and temperature-sensor data to at least one other physically distinct treatment apparatus to facilitate a coordinated treatment between the programmable microcomputer and the at least one other physically distinct treatment apparatus.

11. The apparatus of claim 1, further comprising a communication module located in the apparatus configured to communicate data to a physically distinct computer or a smart phone.

12. The apparatus of claim 1, wherein the apparatus is configured to communicate and coordinate pain treatment with a second physically distinct apparatus, further configured to maintain a program tracking log of treatment time, actual temperature obtained, tension levels, vibration events, and settings.

13. The apparatus of claim 1, further comprising a plurality of ventilation holes in said support band member adapted to release excess heat and body moisture.

14. The apparatus of claim 1 wherein the synchronization assembly is capable of communicating with another apparatus having a second Peltier device to provide coordinated operation of the Peltier device and the second Peltier device.

15. The apparatus of claim 14, wherein the second Peltier device is adapted to produce a second series of temperature patterns.

16. An apparatus for treating pain in an area of a human body by creating a series of temperature patterns on a surface of the human body over a treatment area, said apparatus comprising:
a thermal conduction member;
a power source;
a Peltier device for producing a temperature change in response to an electrical input, said Peltier device disposed on said thermal conduction member;
a metallic member interposed between said Peltier device and said thermal conduction member;
a heat sink member disposed on said Peltier device;
a programmable microcomputer connected to the power source and the Peltier device, the programmable microcomputer adapted to control application of power to the Peltier device so as to control heating and cooling of the Peltier device, wherein control by the programmable microcomputer is achieved by generating power signals which have varying pulse trains of predetermined power and modulation levels, and wherein said programmable microcomputer is configured to control the Peltier device to produce the series of temperature patterns which can be applied to said treatment area, wherein a first predetermined temperature pattern of the series of temperature patterns comprises a first predetermined time period of warm temperature of a first predetermined intensity, and a second predetermined time period of cool temperature of a second predetermined intensity;
a synchronization assembly coupled to the programmable microcomputer and the Peltier device, said synchronization assembly is adapted to coordinate operation so that the first predetermined temperature pattern and a second predetermined temperature pattern of the series of temperature patterns are generated by the programmable microcomputer and provided to the Peltier device, wherein the first predetermined temperature pattern and the second predetermined temperature pattern are alternating with respect to one another, to thus promote blood flow in the treatment area; and
a tension monitoring assembly adapted to be connected to said programmable microcomputer and configured to monitor an amount of tension of a tendon compression band disposed adjacent to the treatment area and to alert a user if the amount of tension exceeds a predetermined level, wherein said tension monitoring assembly is comprised of an optical system with an optical interruption mechanism.

17. The apparatus of claim 16, wherein:
the optical interruption means includes an optical interruption sensor adapted to be connected to said programmable microcomputer, the tendon compression band is configured to support the thermal conduction member over the treatment area and a tendon compression member located away from the treatment area,
the power source is a portable power source, and
said Peltier device and said heat sink member are disposed on an outside surface of the thermal conduction member.

* * * * *